US00PP21817P2

(12) United States Plant Patent
Zaiger et al.

(10) Patent No.: US PP21,817 P2
(45) Date of Patent: Mar. 29, 2011

(54) INTERSPECIFIC TREE NAMED 'BELLA SUN'

(50) Latin Name: *Prunus*
Varietal Denomination: BELLA SUN

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 12/657,172

(22) Filed: Jan. 15, 2010

(51) Int. Cl.
*A01H 5/00* (2006.01)

(52) U.S. Cl. ..... Plt./180

(58) Field of Classification Search ..... Plt./180
See application file for complete search history.

*Primary Examiner* — Annette H Para

(57) ABSTRACT

A new and distinct variety of plumcot tree [*Prunus salicina*× *Prunus armeniaca*]. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. A regular and productive bearer of medium size fruit.
2. Vigorous, upright tree growth.
3. Fruit with very good flavor and eating quality.
4. Producing attractive yellow fruit with a soft red blush.
5. Fruit with a good balance between acid and sugar.

1 Drawing Sheet

Botanical classification: Interspecific *Prunus* species.

BACKGROUND OF THE VARIETY

Field of the Invention

In the field of plant genetics, we conduct an extensive and continuing plant-breeding program including the organization and asexual reproduction of orchard trees, of which plums, peaches, nectarines, apricots, cherries, almonds and interspecifics are exemplary. It was against this background of our activities that the present variety of plumcot tree was originated and asexually reproduced by us in our experimental orchard located near Modesto, Stanislaus County, Calif.

PRIOR VARIETIES

Among the existing varieties of plum and apricot trees, which are known to us, and mentioned herein, are the proprietary selected plum seedling '35EA376, 'Red Beaut' Plum (U.S. Plant Pat. No. 2,539), 'Poppy' Apricot (U.S. Plant Pat. No. 9,593) 'Cot-N-Candy' Interspecific (U.S. Plant Pat. No. 17,827).

STATEMENT REGARDING FEDERALLY SPONSORED RESEARCH AND DEVELOPMENT: Not applicable.

ORIGIN OF THE VARIETY

The new and distinct variety of interspecific plumcot tree, [*Prunus salicina*×*Prunus armeniaca*] was originated by us from a first generation cross between the proprietary plum seedling (35EA376) cross with 'Poppy' Apricot (U.S. Plant Pat. No. 9,593). We selected the proprietary seedling selection (35EA376) from seed of an open pollinated seedling grown from 'Red Beaut' Plum (U.S. Plant Pat. No. 2,539). A large number of these first generation seedlings, growing on their own root system, were budded to older trees of 'Nemaguard' Rootstock (non-patented) to induce earlier maturity and fruit evaluation. Under close observation the present plumcot seedling exhibited desirable fruit characteristics and was selected by us in 2003 for additional asexual propagation and commercialization.

ASEXUAL REPRODUCTION OF THE VARIETY

Asexual reproduction of the new and distinct variety of plumcot tree was by budding to 'Nemaguard' Rootstock (non-patented) as performed by us in our experimental orchard located near Modesto, Calif., and shows reproductions run true to the original tree and all characteristics of the tree and its fruit are established and transmitted through succeeding asexual propagations.

SUMMARY OF THE NEW VARIETY

The new variety of interspecific plumcot tree [Plum×Apricot] is of large size, vigorous upright growth and a productive and regular bearer of medium size, yellow flesh, clingstone fruit with very good flavor and eating quality. The fruit is further characterized by having very short, soft pubescence similar to an apricot, being nearly globose in shape with good storage and shelf life. In comparison to its plum seed parent '35EA376', the new plumcot has pubescent yellow orange skin compared to red slick skin and is 15 days later in maturity. In comparison to its pollen parent 'Poppy' Apricot (U.S. Plant Pat. No. 9,593), the new variety is clingstone compared to freestone, has improved eating quality with a good balance between acid and sugar and is approximately 26 days later in maturity.

PHOTOGRAPH OF THE VARIETY

The accompanying color photographic illustration shows typical specimens of the foliage and fruit of the present new plumcot variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 8 year old tree and the colors are as nearly true as is reasonably possible in a color representation of this type.

DESCRIPTION OF THE VARIETY

The following is a detailed botanical description of the new variety of plumcot tree, its flowers, foliage and fruit, as based on observations of 8 year old specimens grown near Modesto, Calif., with color in accordance with Munsell Book of Color.

Tree:

*Size.*—Large, pruned to 3 to 3.5 meters in height for economical harvesting of fruit. Average width of 3 meters, varies with cultural practices.

*Vigor.*—Vigorous, tree growth of approximately 1.5 to 2 meters the first growing season, varies with soil type, fertility and cultural practices.

*Form.*—Upright, usually pruned to vase shape.

*Branching habit.*—Upright, crotch angle approximately 30° , increases with heavy crop load.

*Productivity.*—Productive, thinning and spacing of fruit necessary for desirable market size. Fruit set varies with climatic conditions at bloom time.

*Bearer.*—Regular, adequate fruit set 6 consecutive years. No alternate bearing observed.

*Fertility.*—Self sterile, pollinator required.

*Density.*—Medium dense, usually pruned to vase shape to increase sunlight to center of tree to enhance fruit color and health of fruit spurs.

*Hardiness.*—Hardy in all stone fruit growing areas of California. Tree grown in USDA Hardiness Zone 9. Winter chilling requirement approximately 650 hours at or below 45° F.

Trunk:

*Size.*—Medium. Average circumference 41.5 cm at 25.1 cm above ground level on a 8 year old tree.

*Stocky.*—Medium, increases with age of tree.

*Texture.*—Medium shaggy, roughness increase with age.

*Color.*—Varies from 10YR 5/2 to 10YR 2/2.

Branches:

*Size.*—Medium. Average circumference 14.2 cm at 1.2 meters above ground on a 8 year old tree. Crotch angle approximately 30°, increases with heavy crop load.

*Surface texture.*—New growth relatively smooth. Mature growth medium rough, roughness increases with age.

*Lenticels.*—Size — medium. Average number 46 in a 25.8 sq cm surface of branch. Average length 4.4 mm. Average width 2.4 mm. Color varies from 10YR 6/8 to 10YR 6/10.

*Color.*—New growth varies from 5GY 5/6 to 5R 3/6. Mature growth varies from 10YR 3/4 to 2.5Y 3/4, varies with age of growth.

Leaves:

*Size.*—Medium. Average length 73.1 mm. Average width 48.6 mm.

*Form.*—Elliptic.

*Apex.*—Cuspidate.

*Base.*—Obtuse.

*Margin.*—Serrate.

*Thickness.*—Medium.

*Surface texture.*—Upper surface relatively smooth, slightly indented over midrib and leaf vein, glabrous. Lower surface relatively smooth, small ridges created by midrib and pinnate venation, glabrous.

*Petiole.*—Size — medium. Average length 17.9 mm. Average width 1.2 mm. Color varies from 2.5GY 5/6 to 7.5R 4/8. Longitudinally grooved. Surface — glabrous.

*Glands.*—Type — globose. Size — small. Average length 0.6 mm. Average diameter 0.3 mm. Average number 4, varies from 3 to 6. Located primarily on the upper portion of petiole and the base of leaf blade. Color varies from 2.5GY 6/6 to 2.5GY 6/8.

*Color.*—Upper surface varies from 5GY 3/6 to 7.5GY 3/6. Lower surface varies from 7.5GY 4/4 to 7.5GY 5/4. Midrib color varies from 5GY 8/4 to 5GY 7/6.

Flowers buds:

*Size.*—Small to medium. Average length 10.9 mm. Average diameter 7.2 mm.

*Hardiness.*—Hardy with respect to California winters.

*Form.*—Conical, slightly elongated before opening.

*Pedicel.*—Average length 4.8 mm. Average width 0.9 mm. Color varies from 2.5GY 7/6 to 5GY 4/6.

*Color.*—N 9.5/ (white).

Flowers:

*Blooming period.*—Date of First Bloom Mar. 1, 2009. Date of Petal Fall Mar. 11, 2009, varies slightly with climatic conditions.

*Size.*—Medium. Average height 13.4 mm. Average diameter 23.8 mm.

*Petals.*—Normally 5, alternately arranged to sepals. Average length 10.9 mm. Average width 11.7 mm. Form — orbicular. Margin — entire. Color N 9.5/ (white). Both surfaces glabrous.

*Sepals.*—Number — normally 5, alternately arranged to petals. Size — small. Average length 3.5 mm. Average width 4.0 mm. Form — triangular. Margin — entire. Both surfaces glabrous. Color — upper surface varies from 2.5Y 6/6 to 2.5GY 6/8, apex with 2.5R 4/10. Lower surface varies from 2.5GY 6/6 to 5GY 6/6, apex with 2.5R 4/10.

*Stamens.*—Average number per flower 33. Average filament length 9.7 mm. Filament color N 9.5/ (white). Anther color varies from 5Y 8/6 to 7.5Y 8/6.

*Pollen.*—Self sterile, pollinator required. Color varies from 5Y 7/8 to 5Y 7/10.

*Pistil.*—Normally one. Surface — pubescent. Average length 12.4 mm. Stigma height relatively even with anthers. Color varies from 10Y 8/4 to 2.5GY 8/6.

*Fragrance.*—Slight aroma.

*Color.*—N 9.5/ (white).

*Number flowers per flower bud.*—Average number 2, varies from 1 to 3.

*Pedicel.*—Average length 6.2 mm. Average width 1.0 mm. Color varies from 10Y 7/6 to 2.5GY 7/8. Surface glabrous.

Fruit:

*Maturity when described.*—Firm ripe.

*Date of first picking.*—Jun. 10, 2009.

*Date of last picking.*—Jun. 22, 2009, varies slightly with climatic conditions.

*Size.*—Medium. Average diameter axially 47.6 mm. Average transversely in suture plane 54.3 mm. Average weight 88 grams, varies slightly with fertility of the soil, amount of thinning and climatic conditions.

*Form.*—Globose, slightly flattened at base and apex.
*Suture.*—Shallow, extends from base to apex.
*Ventral surface.*—Nearly smooth.
*Apex.*—Varies from slightly retuse to nearly round.
*Base.*—Varies from flat to slightly retuse.
*Stem cavity.*—Varies from rounded to slightly elongated in suture plane. Average depth 6.6 mm. Average diameter 10.9 mm.

Stem:
*Size.*—Medium. Avearge length 10.7 mm. Average diameter 2.6 mm.
*Color.*—Varies from 2.5GY 5/6 to 10YR 4/4.

Flesh:
*Ripens.*—Evenly.
*Texture.*—Firm, smooth texture.
*Fibers.*—Few, small, tender.
*Firmness.*—Firm, similar to firmness of the 'Cot-N-Candy' Interspecific (U.S. Plant Pat. No. 17,827).
*Aroma.*—Slight.
*Amydgalin.*—Undetected.
*Eating quality.*—Very good.
*Flavor.*—Very good, good balance between acid and sugar.
*Juice.*—Moderate to heavy, enhances flavor.
*Brix.*—Average 16.9°, varies slightly with amount of fruit per tree and climatic conditions.
*Color.*—Yellow, varies from 2.5Y 8/10 to 5Y 8/10. Pit cavity varies from 2.5Y 8/10 to 5Y 7/10.
*Stone cavity.*—Shape — ovoid. Average length 25.4 mm. Average width 21.3 mm.

Skin:
*Thickness.*—Medium.
*Surface.*—Smooth.
*Pubescence.*—Moderate amount, very short in length.
*Tendency to crack.*—None.
*Color.*—Ground color yellow, varies from 2.5Y 8/10 to 5Y 8/8. Light blush where exposed to sun, color varies from 7.5R 4/10 to 7.5R 4/12.
*Tenacity.*—Tenacious to flesh.
*Astringency.*—None.

Stone:
*Type.*—Clingstone.
*Size.*—Medium. Average length 23.2 mm. Average width 19.4 mm. Average thickness 11.2 mm.
*Form.*—Ovoid.
*Base.*—Relatively flat, varies from flat to slightly rounded.
*Apex.*—Very slightly pointed. Average length 0.2 mm.
*Surface.*—Slightly pitted throughout, a small groove on each side of suture plane.
*Sides.*—Unequal, one side extending slightly further from suture plane.
*Ridges.*—A small ridge on each side of suture plane, extending from base to apex.
*Tendency to Split.*—None.
*Color.*—Varies from 10YR 7/8 to 10YR 6/8.

Kernel:
*Size.*—Small to medium. Average length 15.0 mm. Average width 10.5 mm. Average depth 5.7 mm.
*Form.*—Ovate.
*Viability.*—Viable, complete embryo development.
*Skin color.*—Varies from 2.5Y 8.5/4 to 5Y 9/4.

Use: Dessert.
*Market.*—Local and long distance.

Keeping quality: Good, held firm in cold storage 2 weeks at 38° to 42° without shriveling, internal breakdown of flesh or appreciable loss of eating quality.

Shipping quality: Good, showed minimal skin scarring or bruising during picking, packing or shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of plumcot tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of plumcot tree, substantially as illustrated and described.

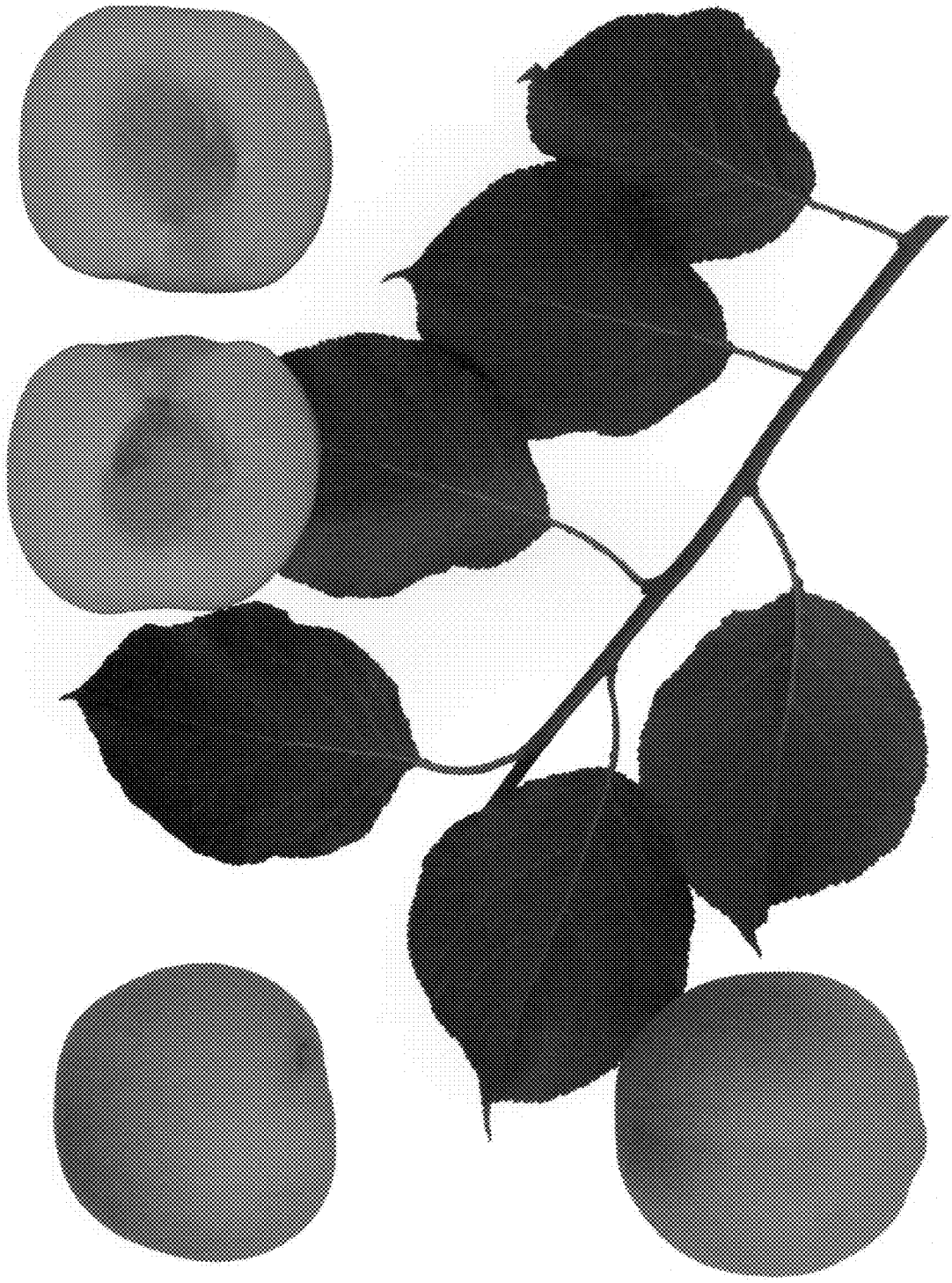

* * * * *